United States Patent [19]

Matson et al.

[11] Patent Number: 6,080,863
[45] Date of Patent: Jun. 27, 2000

[54] PROCESS FOR PRODUCING PIPERIDINE

[75] Inventors: Michael S. Matson; Michael D. Mitchell, both of Bartlesville, Okla.

[73] Assignee: Phillips Petroleum Company, Bartlesville, Okla.

[21] Appl. No.: 09/320,155

[22] Filed: May 26, 1999

[51] Int. Cl.[7] .................. C07D 211/02; C07D 211/04
[52] U.S. Cl. ............................ 546/185; 546/184
[58] Field of Search ...................... 546/185, 184

[56] References Cited

U.S. PATENT DOCUMENTS 4,191,828  3/1980  Horgan et al. ..................... 546/185
4,544,749  10/1985  Ayusawa et al. .................. 546/184
4,605,742  8/1986  Mori et al. ......................... 546/184
5,606,064  2/1997  Lensky ............................... 546/185

*Primary Examiner*—Alan L. Rotman
*Assistant Examiner*—Rita Desai
*Attorney, Agent, or Firm*—Jeffrey R. Anderson

[57] ABSTRACT

A process for activating a hydrogenation catalyst in the presence of an activation agent containing a piperidine compound is disclosed. The thus-activated hydrogenation catalyst is employed as a hydrogenation catalyst in the hydrogenation of a pyridine compound to a piperidine compound.

22 Claims, No Drawings

PROCESS FOR PRODUCING PIPERIDINE

The invention relates to an improved process for the hydrogenation of pyridine compounds to produce piperidine compounds. In another aspect, the invention relates to an improved process for activating a hydrogenation catalyst used for the hydrogenation of pyridine compounds to produce piperidine compounds.

BACKGROUND OF THE INVENTION

It is well known by those skilled in the art that pyridine compounds an be hydrogenated over catalysts comprising a Group VIII metal including iron, cobalt, nickel, ruthenium, rhodium, palladium, osmium, iridium and platinum, particularly in solvents and/or acid solutions. Rhodium is the most active Group VIII metal under acidic conditions. Nickel requires the use of high temperatures (120–175° C.) and high pressures (70–150 atmospheres). Also, use of a nickel catalyst in an alcoholic solvent can result in N-alkylation (alkylation at the nitrogen (N) site) of the piperidine compound producing an undesirable N-alkylation product. The use of ruthenium in aqueous solvents is reported to require temperatures in excess of 100° C. and pressures of about 70 atmospheres, but produces little if any N-alkylation product. To obtain high reactor volume productivity and the most economical and efficient process for converting pyridine compounds to piperidine compounds, it is desirable to hydrogenate pyridine compounds in the absence of any solvent or acid solution, and at the lowest possible temperature and pressure. Also, it is desirable to use a hydrogenation catalyst that is not costly and can be used to produce a sufficient quantity of piperidine compounds per quantity of pyridine compounds such that the cost of the hydrogenation catalyst is low compared to the other costs associated with the hydrogenation process. In addition, it is desirable to improve processes for the hydrogenation of pyridine compounds by minimizing the batch times for hydrogenating pyridine compounds and by minimizing the production of undesirable compounds such as heavies and n-amylamine. Heavies, as used herein, is defined to include N-alkylated piperidines and associated hydrogenolysis products and bipiperidine derivatives.

SUMMARY OF THE INVENTION

It is an object of this invention to provide an improved process for the hydrogenation of a pyridine compound to a piperidine compound in the substantial absence of a solvent and/or acid solution.

It is another object of this invention to provide an improved process for the activation of a hydrogenation catalyst used for hydrogenating a pyridine compound to a piperidine compound.

It is another object of this invention to provide an improved process for the hydrogenation of a pyridine compound to a piperidine compound such that the average batch time is minimized.

It is still another object of the present invention to provide an improved process for the hydrogenation of a pyridine compound to a piperidine compound at reduced pressure.

It is yet another object of the present invention to provide an improved process for the hydrogenation of a pyridine compound to a piperidine compound using an activated hydrogenation catalyst wherein the activated hydrogenation catalyst can be reused at least 30 times.

It is still another object of the present invention to provide an improved process for the hydrogenation of a pyridine compound to a piperidine compound wherein the production of heavies is minimized.

It is another object of the present invention to provide an improved process for the hydrogenation of pyridine

to piperidine

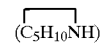

wherein the production of n-amylamine ($C_5H_{11}N$ $H_2$) is minimized.

In accordance with this invention a process for activating a hydrogenation catalyst, used for hydrogenating at least a portion of a hydrocarbon feedstock comprising a pyridine compound, comprises:

a) combining an activation agent comprising a piperidine compound with the hydrogenation catalyst to form a mixture;

b) activating the hydrogenation catalyst in the mixture in the presence of hydrogen and under activation conditions including a temperature in the range of from about 80° C. to about 180° C., a pressure in the range of from about 10 atm to about 30 atm and a time period greater than about 10 minutes, to thereby produce an activated hydrogenation catalyst; and c) separating at least a portion of the activation agent from the activated hydrogenation catalyst.

The thus-activated hydrogenation catalyst can be used in the hydrogenation of pyridine compounds to piperidine compounds by contacting, under conversion conditions, a hydrocarbon feedstock comprising at least one pyridine compound with the inventive activated hydrogenation catalyst.

Other objects and advantages of the invention will become apparent from the detailed description and the appended claims.

DETAILED DESCRIPTION OF THE INVENTION

The hydrogenation catalyst useful in the inventive process can comprise any hydrogenation catalyst which is effective in the hydrogenation of at least a portion of a pyridine compound to produce a piperidine product comprising a piperidine product compound. The pyridine compound can comprise a compound selected from the group consisting of pyridine, at least one pyridine derivative, and combinations of any two or more thereof; wherein the pyridine derivative comprises pyridine substituted with at least one radical selected from the group consisting of an alkyl, a cycloalkyl, an aryl, an alkylaryl, a cycloalkylaryl, and combinations of any two or more thereof. The piperidine product compound can comprise a compound selected from the group consisting of piperidine, at least one piperidine derivative, and combinations of any two or more thereof, wherein the piperidine derivative comprises piperidine substituted with at least one radical selected from the group consisting of an alkyl, a cycloalkyl, an aryl, an alkylaryl, a cycloalkylaryl, and combinations of any two or more thereof.

The hydrogenation catalyst more particularly comprises, consists essentially of, or consists of ruthenium and a support selected from the group consisting of alumina, activated carbon and combinations thereof.

Some examples of suitable compositions useful as the hydrogenation catalyst in the inventive process which are commercially available are set forth in Table I.

TABLE I

| Company | Product Designation | Type |
|---|---|---|
| Sigma - Aldrich | 28,147 - 6 | Ruthenium on activated carbon |
| Degussa Corp. | H101B 3MLE58 | Ruthenium on activated carbon |
| Johnson Matthey, Inc. | C 2095 | Ruthenium on activated carbon |
| Precious Metals Corp. | 12348 | Ruthenium on activated carbon |
| Strem Chemicals, Inc. | 44-4050 | Ruthenium on activated carbon |
| Engelhard Corp. | ESCAT ™ 440 | Ruthenium on activated carbon |

These compositions typically contain about 5 weight percent ruthenium on a dry basis and usually contain about 50 weight percent water, based on the total weights of the compositions.

The use of a hydrogenation catalyst comprising ruthenium in the hydrogenation of a pyridine compound does not require the use of solvents, such as alcohol, nor the use of an acid solution and does not require the pyridine compound to be in the form of its salt to avoid deactivation of the hydrogenation catalyst, all of which are required with the use of other hydrogenation catalysts comprising metals such as platinum, rhodium and nickel.

One key aspect of the invention is the use of an improved process for activating the hydrogenation catalyst. The improvement involves treatment of the catalyst in the presence of an activation agent comprising a piperidine compound, which can be the same as the piperidine product compound described above. The activation agent can also include a composition selected from the group consisting of hydrocarbon solvents, a pyridine compound and combinations of any two or more thereof. The hydrocarbon solvents can comprise hexane or cyclohexane, or any other hydrocarbon that is a solvent for piperidine compounds and that is easily separated from piperidine compounds by distillation.

The hydrogenation catalyst can be combined with the activation agent to form a mixture. The hydrogenation catalyst of the mixture can be activated in the presence of hydrogen and under activation conditions sufficient to produce an activated hydrogenation catalyst which, when used in the hydrogenation of a hydrocarbon feedstock comprising a pyridine compound, results in the conversion of at least a portion of the hydrocarbon feedstock to a piperidine product comprising a piperidine product compound.

The activation conditions more particularly include a temperature in the range of from about 80° C. to about 180° C., preferably from about 100° C. to about 140° C., and most preferably from 120° C. to 130° C.; a pressure in the range of from about 10 atmospheres (atm) to about 40 atm, preferably from about 15 atm to about 30 atm, and most preferably from 20 atm to 30 atm; and a time period greater than about 10 minutes (min), preferably in the range of from about 20 min to about 250 min, and most preferably from 30 min to 200 min.

The amount of activation agent combined with the hydrogenation catalyst can be the same as, or a fraction of, the normal amount of pyridine compounds contacted with the hydrogenation catalyst in the hydrogenation of pyridine compounds.

At least a portion of the activation agent is separated from the activated hydrogenation catalyst. The activated hydrogenation catalyst is then contacted with the hydrocarbon feedstock comprising a pyridine compound, described above, in the presence of hydrogen, preferably in the substantial absence of a solvent and/or an acid solution, and at conversion conditions sufficient to convert at least a portion of the hydrocarbon feedstock to a piperidine product comprising a piperidine product compound, described above.

The conversion conditions more particularly include a temperature in the range of from about 100° C. to about 160° C., preferably from about 100° C. to about 150° C., and most preferably from 110° C. to 145° C.; a pressure in the range of from about 10 atm to about 40 atm, perferably from about 15 atm to about 30 atm, and most preferably from 20 atm to 30 atm.

The contacting of the activated hydrogenation catalyst with the hydrocarbon feedstock can be carried out as a batch-type process or in continuous flow mode. The contacting is preferably performed as a batch-type process wherein the time period for substantially complete hydrogenation is less than about 30 hours, preferably less than about 20 hours, and most preferably less than 15 hours.

The concentration of undesirable heavies produced in the hydrogenation of the hydrocarbon feedstock is preferably less than about 1.0 weight percent, more preferably less than about 0.45 weight percent, and most preferably less than 0.40 weight percent.

In the case where the pyridine compound is pyridine, the pyridine can be obtained from a variety of sources such as Sigma-Aldrich; Burdick and Jackson, Inc.; Fisher Scientific Company; Penta Manufacturing Company; Reilly Industries, Inc.; Nepera, Inc.; and Spectrum Bulk Chemicals, Division of Spectrum Quality Products, Inc.; and can be of varying grades of purity, such as, ACS Grade (99.9% purity), 1° Pyridine (99.5% purity) or technical grade (98% purity). Higher purity pyridine will result in faster reaction rates, especially when the hydrogenation catalyst is activated in piperidine.

In addition, where the pyridine compound is pyridine, the piperidine product can comprise n-amylamine, an undesirable impurity. The concentration of n-amylamine produced in the hydrogenation of the hydrocarbon feedstock is preferably less than about 0.100 weight percent, more preferably less than about 0.090 weight percent, and most preferably less than 0.070 weight percent.

Using the inventive hydrogenation catalyst activation process, the activated hydrogenation catalyst can be used for the hydrogenation of a pyridine compound in at least 30 batches, preferably at least 40 batches, and most preferably at least 50 batches.

EXAMPLES

Test hydrogenation reactions were performed in 300 cc autoclave reactors, each equipped with variable speed mixing, internal heating/cooling coils, a thermowell and a dip tube fitted with a sintered metal frit at the bottom of the tube. The dip tube was connected to an external three-way valve and used to add hydrogen to the reactor through the sintered metal frit or to remove liquid samples through the frit while keeping the catalyst in the reactor. The hydrogen was added on demand to the reactor from a calibrated pressure vessel through a pressure regulator set at the desired reaction pressure. A remote pressure sensor was used to monitor the pressure drop in the calibrated pressure vessel which was therefor a measure of the amount of hydrogen consumed in the reaction.

In a typical charge, 1.25 grams (dry weight) of hydrogenation catalyst was charged to the reactor along with 150 cc of pyridine. The reactor was then sealed and purged with nitrogen and then with hydrogen. The reactor was heated to the desired temperature and hydrogen pressure was added to the desired level, usually about 27 atm. As the hydrogenation proceeded, the pressure of the calibrated pressure vessel was monitored. When the rate of change of the pressure drop reached zero, the reaction was sampled to verify the hydrogenation of pyridine was complete. The reaction mixture was cooled to about 40–50° C. and removed from the reactor through the dip tube. The catalyst and a heel of about 60 cc of crude piperidine remained in the reactor.

An additional amount of pyridine, usually about 140 cc, was then added through a port in the reactor and the hydrogenation step repeated.

When runs were performed following activation using a non-pure pyridine activation agent, the activation was performed by charging the hydrogenation catalyst and activation agent to the reactor using the same procedure described above. The reactor was purged and heated to the desired temperature and then pressured to about 27 atm with hydrogen. The temperature was maintained for a set time period in the range of from about 0.85 to about 1.0 hour. The reactor was then cooled and the activation agent removed through the dip tube and pyridine charged to the reactor as described above. Test data from each Example are summarized in Table 2.

The following catalysts were used as hydrogenation catalysts in the hydrogenation of pyridine.

Catalyst A—5% ruthenium (on a dry basis) on activated carbon obtained from Degussa Corp. under product designation H101B.

Catalyst B—5 wt. % ruthenium (on a dry basis) on activated carbon obtained from Degussa Corp. under product designation 3MLE58.

Catalyst C—5 wt. % ruthenium (on a dry basis) on activated carbon obtained from Johnson Matthey, Inc. under product designation C 2095.

Catalyst D—5 wt. % ruthenium (on a dry basis) on activated carbon obtained from Precious Metals Corp. under product designation 12348.

In Examples 1–5 a first lot of pyridine of 1° grade was used.

Example 1

A 1.25 gram quantity (dry weight) of Catalyst A was charged to the reactor along with 150 cc of pyridine. The activation was performed at 160° C. and about 27 atm and required 2.60 hours to complete. Ten pyridine hydrogenation batches were run at 140° C. with the catalyst activated in this manner. The average batch time was 3.26 hours, the average amount of n-amylamine (nAA) produced was 0.117 wt. % and the average amount of heavies produced was 0.525 wt. %.

Example 2

A 1.25 gram quantity (dry weight) of Catalyst A was charged to the reactor along with 105 cc of piperidine and 45 cc of pyridine. The activation was performed at 140° C. and about 27 atm and required 0.85 hour to complete. Fifteen pyridine hydrogenation batches were run at 140° C. with the catalyst activated in this manner. The average batch time was 2.43 hours, the average amount of nAA produced was 0.115 wt. % and the average amount of heavies produced was 0.475 wt. %. This example demonstrates that the presence of some piperidine during activation decreased the batch times of the subsequent runs, but did not have a significant impact on the nAA content.

Example 3

A 1.25 gram quantity (dry weight) of Catalyst A was charged to the reactor along with 150 cc of piperidine. The activation was performed at 140° C. and about 27 atm and required 0.85 hour to complete. Eight pyridine hydrogenation batches were run at 140° C. with the catalyst activated in this manner. The average batch time was 1.39 hours, the average amount of nAA produced was 0.092 wt. % and the average amount of heavies produced was 0.383 wt. %. This example demonstrates that activation of the catalyst in only piperidine and hydrogen results in decreased batch times and a decrease in the production of nAA and heavies as compared to activation in pyridine in Example 1 and activation in a piperidine/pyridine mixture in Example 2.

Example 4

A 1.25 gram quantity (dry weight) of Catalyst A was charged to the reactor along with 150 cc of piperidine. The activation was performed at 130° C. and about 27 atm and required 0.85 hour to complete. Twenty-three pyridine hydrogenation batches were run at 130° C. with the catalyst activated in this manner. The average batch time was 2.11 hours, the average amount of nAA produced was 0.077 wt. % and the average amount of heavies produced was 0.373 wt. %. This example shows that activation in piperidine at a lower temperature produces a catalyst that results in batch times that are lower than when the activation is performed in pyridine, but somewhat longer than batch times for catalysts activated in piperidine at 140° C. However, the catalyst activated in piperidine at 130° C. produces less nAA and less heavies than a catalyst activated in piperidine at 140° C.

Example 5

A 1.25 gram quantity (dry weight) of Catalyst A was charged to the reactor along with 75 cc of piperidine (rather than the normal charge of 150 cc). The activation was performed at 110° C. and about 27 atm and required 0.85 hour to complete. Two pyridine hydrogenation batches were run at 110 20 C. with the catalyst activated in this manner. The average batch time was 5.03 hours, the average amount of nAA produced was 0.050 wt. % and the average amount of heavies produced was 0.229 wt. %, substantially reduced from other tests. Five additional pyridine hydrogenation batches were run at 120° C. The average batch time was 3.35 hours, the average amount of nAA produced was 0.062 wt. % and the average amount of heavies produced was 0.325 wt. %. Three additional pyridine hydrogenation batches were run at 130° C. The average batch time was 2.34 hours, the average amount of nAA produced was 0.072 wt. % and the average amount of heavies produced was 0.340 wt. %.

In Examples 6–17 a second lot of pyridine of 1° grade was used.

Example 6

A 1.25 gram quantity (dry weight) of Catalyst A was charged to the reactor along with 150 cc of pyridine. The activation was performed at 150° C. and about 27 atm and required 3.11 hours to complete. Ten pyridine hydrogenation batches were run at 140° C. with the catalyst activated in this manner. The average batch time was 2.64 hours, the average amount of nAA produced was 0.117 wt. % and the average amount of heavies produced was 0.539 wt. %. Although this source of pyridine hydrogenates slightly faster, the amount of nAA and heavies produced is essentially the same as that produced using the other pyridine source in Example 1.

Example 7

A 1.25 gram quantity (dry weight) of Catalyst A was charged to the reactor along with 150 cc of piperidine. The activation was performed at 130° C. and about 27 atm and required 0.85 hour to complete. Twelve pyridine hydrogenation batches were run at 130° C. with the catalyst activated in this manner. The average batch time was 1.65 hours, the average amount of nAA produced was 0.070 wt. % and the average amount of heavies produced was 0.315 wt. %. This example, as compared to Example 3, demonstrates that pyridine from two different lots respond similarly when the hydrogenation catalyst is activated in piperidine and hydrogen.

Example 8

A 0.63 gram quantity (dry weight) of Catalyst A was charged to the reactor along with 75 cc of piperidine. The activation was performed at 130° C. and about 27 atm and required 1.0 hour to complete. Five pyridine hydrogenation batches were run at 130° C. with the catalyst activated in this manner. The average batch time was 3.81 hours, the average amount of nAA produced was 0.069 wt. % and the average amount of heavies produced was 0.319 wt. %. The batch time was substantially longer than when twice the amount of catalyst was used in Example 7 (3.81 hours vs. 1.65 hours). The nAA and heavies content, however, were reduced over Example 6 because of the piperidine activation.

Example 9

A 1.25 gram quantity (dry weight) of Catalyst A was charged to the reactor along with 50 cc of cyclohexane and 25 cc of piperidine. The activation was performed at 130° C. and about 27 atm and required 1.0 hour to complete. Eleven pyridine hydrogenation batches were run at 130° C. with the catalyst activated in this manner. The average batch time was 1.83 hours, the average amount of nAA produced was 0.082 wt. % and the average amount of heavies produced was 0.349 wt. %. This example demonstrates that the catalyst can be activated in piperidine diluted with an inert hydrocarbon.

Example 10

A 1.25 gram quantity (dry weight) of Catalyst A was charged to the reactor along with 150 cc of cyclohexane. The activation was performed at 130° C. and about 27 atm and required 1.0 hour to complete. Three pyridine hydrogenation batches were run at 130° C. with the catalyst activated in this manner. The average batch time was 3.53 hours vs. 1.65 hours when the catalyst was activated in piperidine in Example 7. The average amount of nAA produced was 0.106 wt. % which is only slightly better than expected for catalyst activated in pyridine (Example 6), but not nearly as low as that observed for activation in piperidine in Example 7. The average amount of heavies produced was 0.452 wt. %. This example further demonstrates the unique results obtained by activation in piperidine of reduced average batch time, reduced nAA production and reduced heavies production.

Example 11

A 1.25 gram quantity (dry weight) of Catalyst A was charged to the reactor along with 150 cc of piperidine. The activation was performed at 130° C. and about 27 atm in a hydrogen free atmosphere and required 1.0 hour to complete. Two pyridine hydrogenation batches were run at 130° C. with the catalyst activated in this manner. The average batch time was 5.34 hours. This is clearly not an improvement in the reaction rate as compared with activation in piperidine and hydrogen in Example 7. The average amount of nAA produced was 0.070 wt. % which is about the same level of reduction obtained with activation in piperidine plus hydrogen in Example 7. The average amount of heavies produced was 0.471 wt. % which is less than that seen for catalyst activated in pyridine in Example 6 (0.539 wt %) but greater than the 0.315 wt. % seen with activation in piperidine plus hydrogen in Example 7. This example clearly demonstrates the advantage of activation with both piperidine and hydrogen of reduced average batch time and reduced heavies production.

Example 12

A 1.25 gram quantity (dry weight) of Catalyst B was charged to the reactor along with 150 cc of pyridine. The activation was performed at 160° C. and about 27 atm and required 2.42 hours to complete. Eight pyridine hydrogenation batches were run at 140° C. with the catalyst activated in this manner. The average batch time was 2.45 hours, the average amount of nAA produced was 0.100 wt. % and the average amount of heavies produced was 0.432 wt. %.

Example 13

A 1.25 gram quantity (dry weight) of Catalyst B was charged to the reactor along with 150 cc of piperidine. The activation was performed at 130° C. and about 27 atm and required 1.0 hour to complete. Five pyridine hydrogenation batches were run at 130° C. with the catalyst activated in this manner. The average batch time was 2.37 hours, the average amount of nAA produced was reduced from 0.100 wt. % in Example 12 to 0.061 wt. % and the average amount of heavies produced was reduced from 0.432 wt. % in Example 12 to 0.270 wt. %.

Example 14

A 1.25 gram quantity (dry weight) of Catalyst C was charged to the reactor along with 150 cc of pyridine. The activation was performed at 160° C. and about 27 atm and required 5.36 hours to complete. This is a very long batch time for a hydrogenation performed at this temperature. Two pyridine hydrogenation batches were run at 140° C. with the catalyst activated in this manner. The average batch time was 5.92 hours, the average amount of nAA produced was 0.117 wt. % and the average amount of heavies produced was 0.592 wt. %.

Example 15

A 1.25 gram quantity (dry weight) of Catalyst C was charged to the reactor along with 150 cc of piperidine. The activation was performed at 130° C. and about 27 atm and required 1.0 hour to complete. Three pyridine hydrogenation batches were run at 130° C. with the catalyst activated in this manner. The average batch time was 3.77 hours which is a considerable reduction in batch time vs. the 5.92 hour average batch time using Catalyst C activated in pyridine in Example 14. The average amount of nAA produced was reduced from 0.117 wt. % in Example 14 to 0.059 wt. % while the average amount of heavies produced were reduced from 0.592 wt. % in Example 14 to 0.371 wt. %. Two additional pyridine hydrogenation batches were run at 140° C. and resulted in an average batch time of 2.60 hours. The average amount of nAA produced rose slightly to 0.071 wt. %, but was much less than the 0.117 wt. % seen in Example 14 with Catalyst C activated in pyridine. The average amount of heavies produced was 0.507 wt. %.

Example 16

A 1.25 gram quantity (dry weight) of Catalyst D was charged to the reactor along with 150 cc of pyridine. The activation was performed at 160° C. and about 27 atm and required 2.73 hours to complete. Three pyridine hydrogenation batches were run at 140° C. with the catalyst activated in this manner. The average batch time was 4.68 hours, the average amount of nAA produced was 0.272 wt. % and the average amount of heavies produced was 0.466 wt. %.

Example 17

A 1.25 gram quantity (dry weight) of Catalyst D was charged to the reactor along with 150 cc of piperidine. The activation was performed at 130° C. and about 27 atm and required 1.0 hour to complete. Two pyridine hydrogenation batches were run at 130° C. with the catalyst activated in this manner. The average batch time was 2.95 hours which is a very significant reduction in batch time vs. the 4.68 hour average batch time using Catalyst D activated in pyridine in Example 16. The average amount of nAA produced was reduced from 0.272 wt. % in Example 16 to 0.096 wt. %. The average amount of heavies produced was reduced from 0.466 wt. % in Example 16 to 0.277 wt. %.

n-amylamine production and reduced heavies production, when such hydrogenation catalysts activated in the presence of such activation agent are used in the hydrogenation of pyridine compounds, as compared to the use of such hydrogenation catalysts which are not activated in the presence of such activation agent.

Reasonable variations, modification and adaptations can be made within the scope of the disclosure and the appended claims without departing from the scope of this invention.

That which is claimed is:

1. A process for activating a hydrogenation catalyst comprising a Group VIII metal selected from the group consisting of iron, cobalt, nickel, ruthenium, rhodium, palladium, osmium, iridium, platinum, and combinations of any two or more thereof which is suitable for use for hydrogenating at least a portion of a hydrocarbon feedstock comprising a pyridine compound, said process comprising the steps of:
   a) combining an activation agent comprising a piperidine compound with said hydrogenation catalyst to form a mixture;
   b) activating said hydrogenation catalyst in said mixture in the presence of hydrogen and under activation conditions including a temperature in the range of from about 80° C. to about 180° C., a pressure in the range of from about 10 atm to about 40 atm and a time period greater than about 10 minutes, to thereby produce an activated hydrogenation catalyst; and
   c) separating at least a portion of said activation agent from said activated hydrogenation catalyst.

2. A process in accordance with claim 1 wherein said hydrogenation catalyst comprises ruthenium and a support

TABLE II

| EX. # | Catalyst | Py[a] Act. Lot | Activation Method[b] Agent | Temp. (° C.) | Time, hours | # of Batches | RXN Temp. ° C. | Avg. Batch Time, hours | wt. % nAA | wt. % Heavies |
|---|---|---|---|---|---|---|---|---|---|---|
| 1 | A | 1 | Py | 160 | 2.60 | 10 | 140 | 3.26 | 0.117 | 0.525 |
| 2 | A | 1 | 30% Py/70% Pip | 140 | 0.85 | 15 | 140 | 2.43 | 0.115 | 0.475 |
| 3 | A | 1 | Pip | 140 | 0.85 | 8 | 140 | 1.39 | 0.092 | 0.383 |
| 4 | A | 1 | Pip | 130 | 0.85 | 23 | 130 | 2.11 | 0.077 | 0.373 |
| 5 | A | 1 | Pip @ 50% vol. | 110 | 0.85 | 2 | 110 | 5.03 | 0.050 | 0.229 |
|  |  |  |  |  |  | 5 | 120 | 3.35 | 0.062 | 0.325 |
|  |  |  |  |  |  | 3 | 130 | 2.34 | 0.072 | 0.340 |
| 6 | A | 2 | Py | 150 | 3.11 | 10 | 140 | 2.64 | 0.117 | 0.539 |
| 7 | A | 2 | Pip | 130 | 0.85 | 12 | 130 | 1.65 | 0.070 | 0.315 |
| 8 | A | 2 | Pip @ 50% vol. | 130 | 1.00 | 5 | 130 | 3.81 | 0.069 | 0.319 |
| 9 | A | 2 | CyC6/Pip | 130 | 1.00 | 11 | 130 | 1.83 | 0.082 | 0.349 |
| 10 | A | 2 | CyC6 | 130 | 1.00 | 3 | 130 | 3.53 | 0.106 | 0.452 |
| 11 | A | 2 | Pip/ No H2 | 130 | 1.00 | 2 | 130 | 5.34 | 0.070 | 0.471 |
| 12 | B | 2 | Py | 160 | 2.42 | 8 | 140 | 2.45 | 0.100 | 0.432 |
| 13 | B | 2 | Pip | 130 | 1.00 | 5 | 130 | 2.37 | 0.061 | 0.270 |
| 14 | C | 2 | Py | 160 | 5.36 | 2 | 140 | 5.92 | 0.117 | 0.592 |
| 15 | C | 2 | Pip | 130 | 1.00 | 3 | 130 | 3.77 | 0.059 | 0.371 |
|  |  |  |  |  |  | 2 | 140 | 2.60 | 0.071 | 0.507 |
| 16 | D | 2 | Py | 160 | 2.73 | 3 | 140 | 4.68 | 0.272 | 0.466 |
| 17 | D | 2 | Pip | 130 | 1.00 | 2 | 130 | 2.95 | 0.096 | 0.277 |

Py = pyridine; Pip = piperidine; $C_yC_6$ = cyclohexane
[a]pyridine of 1° grade
[b]Act. Agent = Activation Agent. Normal total volume of Act. Agent = 150 cc.
The activation is normally carried out in the presence of $H_2$ From the data in Table II it is readily apparent that the inventive process of activating hydrogenation catalysts in the presence of an activation agent comprising a piperidine compound results in reduced average batch times, reduced selected from the group consisting of alumina, activated carbon and combinations thereof.

3. A process in accordance with claim 1 wherein said piperidine compound comprises a compound selected from the group consisting of piperidine, at least one piperidine derivative, and combinations of any two or more thereof; and wherein said piperidine derivative comprises piperidine substituted with at least one radical selected from the group consisting of an alkyl, a cycloalkyl, an aryl, an alkylaryl, a cycloalkylaryl, and combinations of any two or more thereof.

4. A process in accordance with claim 1 wherein said activation conditions of said step (b) include a temperature in the range of from about 100° C. to about 140° C., a pressure in the range of from about 15 atm to about 30 atm and a time period in the range of from about 20 minutes to about 250 minutes.

5. A process in accordance with claim 1 wherein said piperidine compound comprises piperidine.

6. A process in accordance with claim 1 wherein said activation agent is characterized further to include a composition selected from the group consisting of hydrocarbon solvents, a pyridine compound and combinations of any two or more thereof.

7. A process in accordance with claim 6 wherein said hydrocarbon solvents comprise cyclohexane.

8. A process for hydrogenating at least a portion of a hydrocarbon feedstock comprising a pyridine compound to a piperidine product comprising a piperidine product compound, said process comprising the steps of:

a) combining an activation agent comprising a piperidine compound with a hydrogenation catalyst comprising a Group VIII metal selected from the group consisting of iron, cobalt, nickel, ruthenium, rhodium, palladium, osmium, iridium, platinum, and combinations of any two or more thereof to form a mixture;

b) activating said hydrogenation catalyst in said mixture in the presence of hydrogen and under activation conditions including a temperature in the range of from about 80° C. to about 180° C., a pressure in the range of from about 10 atm to about 40 atm and a time period in the range of from about 10 minutes to about 300 minutes, to thereby produce an activated hydrogenation catalyst;

c) separating at least a portion of said activation agent from said activated hydrogenation catalyst; and d) thereafter contacting said hydrocarbon feedstock with said activated hydrogenation catalyst in the presence of hydrogen and under conversion conditions to thereby produce said piperidine product.

9. A process in accordance with claim 8 wherein said hydrogenation catalyst comprises ruthenium and a support selected from the group consisting of alumina, activated carbon and combinations thereof.

10. A process in accordance with claim 8 wherein said pyridine compound comprises a compound selected from the group consisting of pyridine, at least one pyridine derivative, and combinations of any two or more thereof; wherein said pyridine derivative comprises pyridine substituted with at least one radical selected from the group consisting of an alkyl, a cycloalkyl, an aryl, an alkylaryl, a cycloalkylaryl and combinations of any two or more thereof.

11. A process in accordance with claim 8 wherein said piperidine compound comprises a compound selected from the group consisting of piperidine, at least one piperidine derivative, and combinations of any two or more thereof; and wherein said piperidine derivative comprises piperidine substituted with at least one radical selected from the group consisting of an alkyl, a cycloalkyl, an aryl, an alkylaryl, a cycloalkylaryl, and combinations of any two or more thereof.

12. A process in accordance with claim 8 wherein said activation conditions of said step (b) include a temperature in the range of from about 100° C. to about 140° C., a pressure in the range of from about 15 atm to about 30 atm and a time period in the range of from about 20 minutes to about 250 minutes.

13. A process in accordance with claim 8 wherein said pyridine compound comprises pyridine.

14. A process in accordance with claim 8 wherein said piperidine compound comprises piperidine.

15. A process in accordance with claim 13 wherein said piperidine product comprises less than about 0.100 weight percent n-amylamine.

16. A process in accordance with claim 8 wherein said activation agent is characterized further to include a composition selected from the group consisting of hydrocarbon solvents, a pyridine compound and combinations of any two or more thereof.

17. A process in accordance with claim 16 wherein said hydrocarbon solvents comprise cyclohexane.

18. A process in accordance with claim 8 wherein said conversion conditions of said step (d) include a temperature in the range of from about 100° C. to about 160° C., a pressure in the range of from about 10 atm to about 40 atm and a time period of less than about 30 hours.

19. A process in accordance with claim 8 wherein said conversion conditions of said step (d) include a temperature in the range of from about 100° C. to about 160° C., a pressure in the range of from about 10 atm to about 40 atm and a time period of less than about 20 hours.

20. A process in accordance with claim 8 wherein said conversion conditions of said step (d) include a temperature in the range of from about 100° C. to about 160° C., a pressure in the range of from about 10 atm to about 40 atm and a time period of less than about 15 hours.

21. A process in accordance with claim 8 wherein said contacting of said hydrocarbon feedstock with said activated hydrogenation catalyst of step (d) is in the substantial absence of a solvent and in the substantial absence of an acid solution.

22. A process in accordance with claim 8 wherein said step (d) is repeated at least about 30 times.

* * * * *